United States Patent [19]

Stokes

[11] 4,313,448

[45] Feb. 2, 1982

[54] MYOCARDIAL SUTURELESS LEAD

[75] Inventor: Kenneth B. Stokes, Brooklyn Park, Minn.

[73] Assignee: Medtronic, Inc., Minneapolis, Minn.

[21] Appl. No.: 115,966

[22] Filed: Jan. 28, 1980

[51] Int. Cl.³ .............................................. A61N 1/04
[52] U.S. Cl. ................................ 128/785; 128/419 P
[58] Field of Search .................... 128/341, 349, 419 P, 128/772, 784–786

[56] References Cited

U.S. PATENT DOCUMENTS

| | | | |
|---|---|---|---|
| 3,216,424 | 11/1965 | Chardack | 128/419 P |
| 3,367,339 | 2/1968 | Sessions | 128/419 P |
| 3,572,344 | 3/1971 | Boldoc | 128/419 P |
| 3,880,169 | 4/1975 | Starr et al. | 128/419 P |
| 4,010,758 | 3/1977 | Rockland et al. | 128/419 P |
| 4,058,128 | 11/1977 | Frank et al. | 128/419 P |
| 4,142,530 | 3/1979 | Witikampf | 128/419 P |

*Primary Examiner*—William E. Kamm
*Attorney, Agent, or Firm*—John L. Rooney; Lew Schwartz; Joseph F. Breimayer

[57] ABSTRACT

Myocardial sutureless unipolar lead including an insulated conductor coil adjacent to a base pad, and a barbed electrode spaced adjacent to the base pad and connected to the conductor coil. The sutureless myocardial unipolar lead requires no stab wound or sutures for electrode placement and support. The barbed electrode is secured to the heart by gently pushing the tip into the myocardial tissue and the electrode is thereby secured to the myocardial tissue. The lead accepts a stiffening stylet for controlling the stiffness to aid in placement of the electrode within the myocardial tissue, and without the need for further insertion tool. The angle of the barbed electrode determines the specific application of the lead for ventricular or atrial pacing applications.

9 Claims, 4 Drawing Figures

MYOCARDIAL SUTURELESS LEAD

BACKGROUND OF THE INVENTION

1. Field of the Invention-The present invention relates to a surgical electrical applicator, and more particularly, pertains to a myocardial sutureless unipolar lead.

2. Description of the Prior Art-Prior art myocardial leads usually have had to be sutured into position which has been difficult to the medical personnel applying the lead to the myocardial tissue. The suturing of the myocardial leads presented surgical problems in the application of the lead. The sutured myocardial leads have been sometimes considered less than desirable in the application of the lead.

Other prior art myocardial leads have required tools for application of the lead in the myocardium. The tools required surgical manipulations by medical personnel applying the leads. The application of the lead required special forceps, or special application tools requiring numerous turns which required medical personnel which were adept in such application of the leads. Also, the leads which required additional tools also required more time for application of the leads, and also a large working area within the area of the heart of the individual patient for application of the leads. Finally, the prior art leads had little or no stretch or flexibility between the electrode and lead itself sometimes resulting in high chronic thresholds. The chronic results were sometimes less than desirable due to the lack of stretch of the lead, especially between the pacing electrode and the distal end of the lead itself.

The present invention overcomes the disadvantages of the prior art myocardial leads by providing a sutureless myocardial unipolar lead which requires no stab wound or sutures for electrode placement and support, and a lead which can be secured to the heart by gently pushing the tip of the barbed electrode into the myocardial tissue. The barbed electrode secures itself in the myocardial tissue.

SUMMARY OF THE INVENTION

The purpose of the present invention is to provide a sutureless myocardial unipolar lead which is safe to apply on the myocardial tissue of the heart, and provides a low profile, light weight electrode head with a small flexible lead behind the barbed electrode itself.

According to one embodiment of the present invention, there is provided a myocardial sutureless unipolar lead including a forward facing barbed electrode having the tip at a predetermined angle with relation to the shank of the electrode, a flexible base pad having a substantially centered hole and a plurality of outer holes for fibrous ingrowth, the shank of the electrode extending up through the substantially centered hole, an insulated conductor coil having a terminal pin at a proximal end and a distal end of a diameter sufficient to accept the shank of the barbed electrode, attachment sleeve for attaching the conductor coil over the electrode shank and insulation over the sleeve securing the distal end of the conductor coil to the flexible base pad whereby the barbed electrode is pushed into the myocardial tissue to the point where the base pad engages against the epi cardial tissue thereby indicating implantation within the myocardial tissue. A stylet can be used in combination with the lead for providing controlled stiffness with the lead. The lead can be used in either ventricular pacing or atrial pacing, depending on the specific angular relationship of the barded electrode with respect to the flexible base pad.

A significant aspect and feature of the present invention is a sutureless myocardial unipolar lead which requires no stab wound or sutures for electrode placement or support. Because of the barbed electrode design configuration, the lead can be secured to the heart by gently pushing the tip into the myocardial tissue. The electrode secures itself to myocardial tissue. The lead is simple to apply to the myocardial tissue and requires no tools. The lead is easy to implant by medical personnel and requires a least amount of time and can be performed under a local anesthetic, such as with a keyhole implantation procedure by using the stylet and forceps, if desired, in limited access areas. A stylet imparts a certain controlled stiffness during implantation.

Another significant aspect and feature of the present invention is a sutureless myocardial unipolar lead which provides better chronic results and is less traumatic to the patient. The lead, due to its unique contruction, reduces high chronic thresholds. One reason is that there is a certain amount of flex-stretchability provided by the configuration of the electrode head and conductor coil which is low profile. This also results in less pericardial rub. The flexible base pad and the conductor coil provides a certain amount of flexibility and stretch, thus reducing high chronic thresholds.

A further significant aspect and feature of the present invention, most importantly, is a sutureless myocardial lead which is easy to install and includes a flexible base pad which provides a stop during insertion, and a controlled predetermined depth of insertion of the barbed electrode thereby preventing punch-through of the myocardial tissue by the barbed electrode. The barbed electrode is also removable by carefully removing and retracting gently the barbed electrode for whatever reason.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the Figures thereof and wherein.

DESCRIPTION OF PREFERRED EMBODIMENTS

Figure 1:
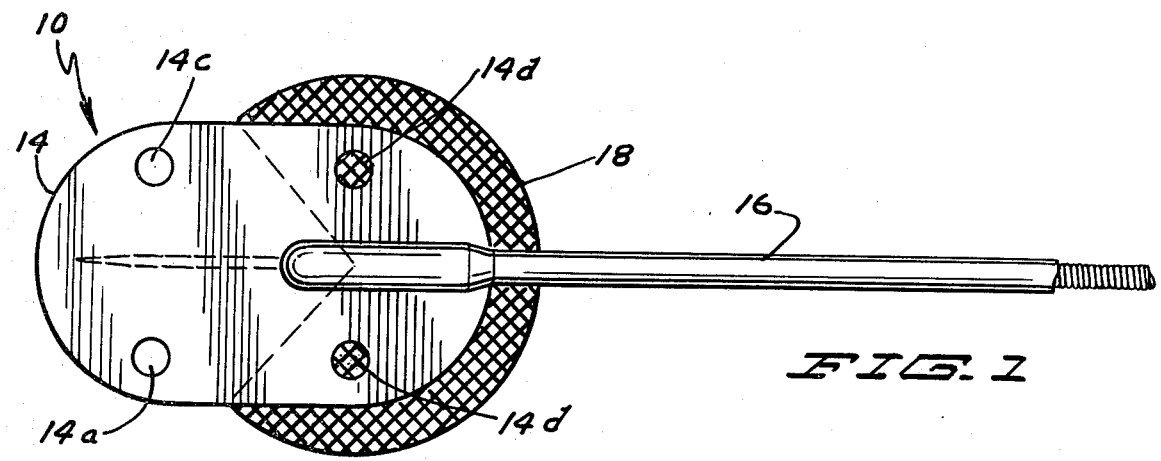
FIG. 1 illustrates a top plan view of a sutureless myocardial unipolar lead, the present invention.
Figure 4:
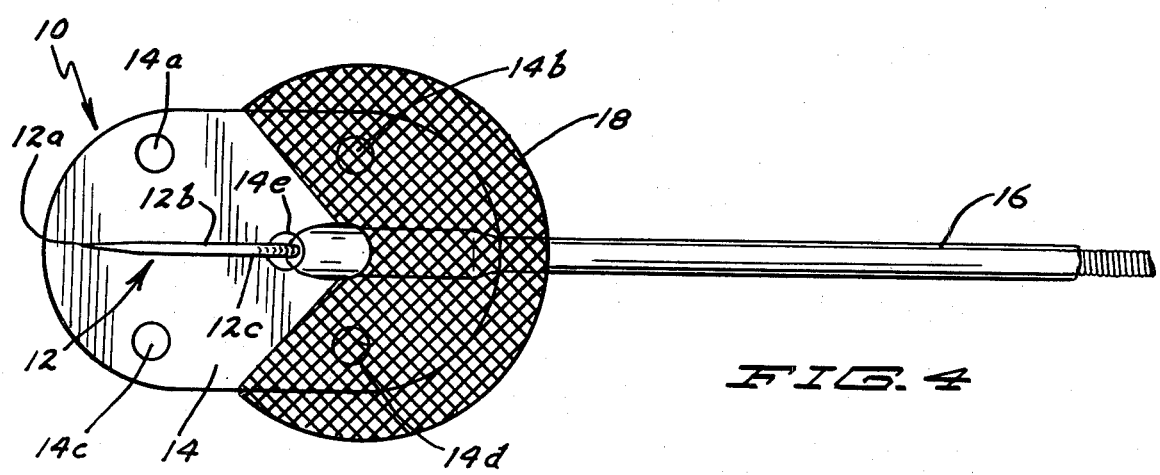
FIG. 4 illustrates a bottom view, identical for FIGS. 2 and 3 of the present invention.

FIG. 1, which illustrates a top plan view of a sutureless myocardial unipolar lead 10, the present invention, shows the lead 10 including a forward facing, in line, spaced barbed electrode 12 on the underside of a flexible base pad 14. The base pad 14 having an elongated rectangular shape with rounded corners includes a plurality of fibrous ingrowth holes 14a–14d. A coiled pacing conductor 16 connects to a shank of the barbed electrode 12 as later described in detail and extends through a substantially centered hole 14e as illustrated in FIG. 4 and is secured to the flexible base pad 14 as later described in detail. The coiled conductor 16 consists of a three or four filar coil made from a silver/MP35 N composite Drawn-Brazed-Strand (DBS) wire which provides for redundant current paths and tolerance to flexural stresses. The coil conductor 16 is encapsulated in polyether urethane elastomer which provides an insulated conductor with stretch and flexibility. A surgical mesh 18 having a circumferential portion running approximately 270° plus or minus 20° from the centered hole 14e surrounds the electrode patch at the centered hole 14e and provides for fibrous ingrowth. Surgical mesh 18 can be affixed to the base pad 14 with suitable adhesive by way of example and for purposes of illustration only.

Figure 2:
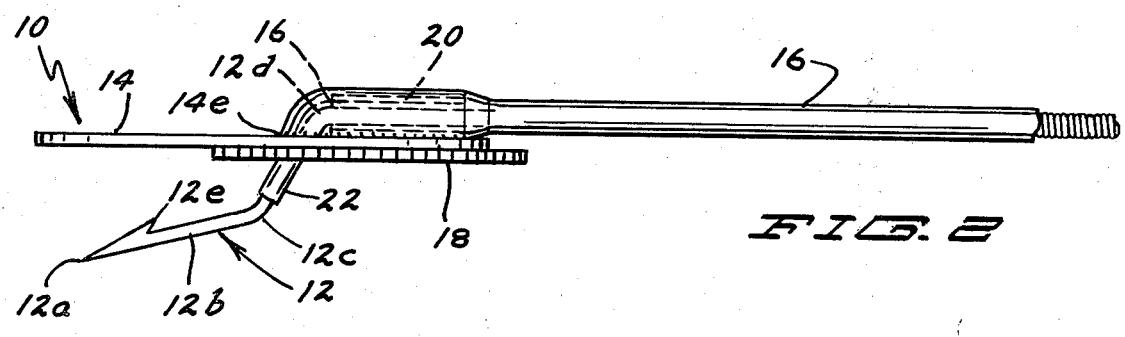
FIG. 2 illustrates a side view of one embodiment of the present invention for ventricular pacing.

FIG. 2, which illustrates a side view of the sutureless myocardial unipolar lead 10 for ventricular use, shows the barbed electrode 12 including a barbed electrode tip 12a, a tip shank 12b, a connecting shank 12c and a substantially horizontal shank end 12d, all connected together thereby forming the barbed electrode 12. The shank end 12d has an outer diameter which is less than the inner diameter of the coiled conductor 16 so that the outer diameter of the shank end 12d is accommodated within the coiled conductor 16. A sleeve 20 engages over the distal end of the coiled conductor 16 and is crimped thereby securing the coiled conductor 16 to the shank 12d of the barbed electrode 12. The assembly of the sleeve 20 and coiled conductor 16 is encapsulated in polyether urethane elastomer to the flexible base pad 14. The angle between the tip shank 12b and connecting shank 12c for ventricular pacing is 135° plus or minus 15°. The diameter of the shanks of the electrode 12 are in the range of twenty thousandths of an inch. The electrode 12 is made of platinum or platinum-iridium. An insulating member 22 surrounds an upper portion of the connecting shank 12c, and can be polyether urethane elastomer which decreases the surface area of the barbed electrode 12 for ventricular pacing.

Figure 3:
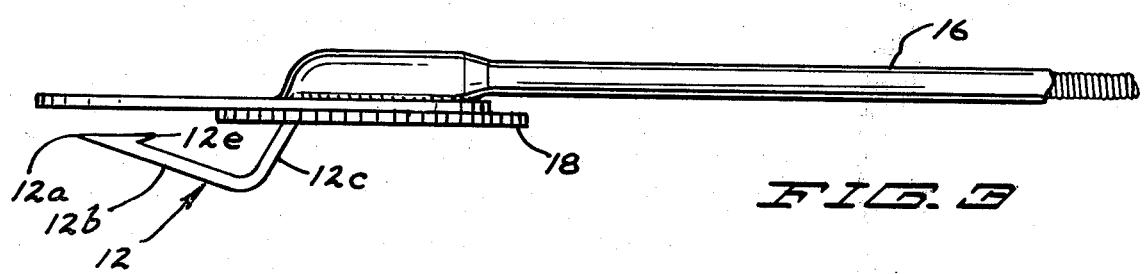
FIG. 3 illustrates a side view of a second embodiment of the present invention for atrial pacing.

FIG. 3, which illustrates a side view of another embodiment of the sutureless myocardial unipolar lead 10, the present invention, for atrial pacing, shows numerals which correspond to those elements previously delineated. The difference is that the angle between the tip shank 12b and connecting shank 12c for atrial pacing is 105° plus or minus 15° and insulation 22 is not required as the barbed electrode operates in smaller tissue. All other numerals correspond to those elements previously delineated.

FIG. 4 shows a bottom view of the sutureless myocardial unipolar lead 10 where all numerals correspond to those elements previously delineated including the insulation member 22 for the ventricular embodiment of FIG. 2.

PREFERRED MODE OF OPERATION

Application of the sutureless myocardial unipolar lead 10 is performed by first providing access to the myocardial tissue, either by keyhole implantation or through the chest of the patient. While tools are not needed to implant the electrode and the electrode can be slid into position without any need of any insertion tool, a stiffening stylet can be slid through the terminal pin of the proximal end providing controlled stiffness imparted by the stylet and forceps can also be used.

The lead 10 can be secured to the heart by gently pushing the barbed electrode tip 12a into the myocardium. The barbed electrode 12 will secure itself to the myocardial tissue. A stylet can be used, and after electrode 12 placement, the stylet is removed leaving a very flexible coil pacing conductor 16. The flexible base pad 14 determines the depth of the barbed electrode tip 12a penetrating into the myocardium, whether the lead be for ventricular pacing of FIG. 2 or atrial pacing of FIG. 3. The lead 10 can also be sutured into position with sutures passing through either the fibrous ingrowth holes 14a-14d or directly through the flexible base pad 14.

The angular relationship of the tip shank 12b with respect to the connecting shank 12c aids in the placement of the barbed electrode 12 in addition to providing for proper depth penetration of the barbed electrode 12 including the rearward extending barb 12e adjacent to barbed electrode tip 12a. For ventricular pacing, the angular relationship provides for penetration at a proper position of the barbed electrode tip 12a, and ease of application, especially when using a stylet or forceps. For atrial pacing, the angular relationship in addition to the above, provides that the barbed electrode tip 12a positions upwardly in the thin wall tissue due to the upward cant of the barbed electrode tip 12a. The barbed electrode tip 12a and the rearward extending barb 12e provide two high current density points for stimulation.

In the event the lead 10 is removed, the lead can be carefully removed by gently retracting the electrode 12.

Various modifications can be made to the sutureless myocardial unipolar lead 10 without departing from the apparent scope of the present invention. While angular relationships have been set forth for ventricular and atrial pacing, these are by way of example and for purposes of illustration only and anything within or near the range is considered within the scope of the present invention. The size of the electrode 12 is a preferred size, but is not to be construed as limiting of the present invention, nor is the size of the flexible base pad 14 or relationship of the coiled conductor 16 to the flexible base pad 14 of the electrode 12.

Having thus described the invention, what is claimed is:

1. A body implantable lead comprising:
 a conductor having a distal end;
 an insulating sheath covering said conductor; means attached to said conductor near said distal end for affixing said body implantable lead to body tissue; and
 flexible base means attached to said conductor near said distal end which in a relaxed state is disposed over said fixation means from at least one direction and which upon application of a small amount of force may be bent back exposing said fixation means from said at least one direction.

2. A body implantable lead according to claim 1 wherein said affixing means further comprises:
 a barbed element having a first pointed distal tip.

3. A body implantable lead according to claim 2 wherein said barbed element has a second pointed tip in a direction opposite of said first pointed tip.

4. A body implantable lead according to claim 3 wherein said first pointed tip and said second pointed tip point in directions parallel to the plane of said flexible base means in said relaxed state.

5. A body implantable lead according to claim 4 wherein said second pointed tip points in a direction toward said flexible base means.

6. A body implantable lead according to claim 2 wherein said first pointed tip points in a direction away from said flexible base means.

7. A body implantable lead according to claim 2, 3, 4, 6 or 5 wherein said first pointed tip points in a direction distal of said conductor.

8. A body implantable lead according to claim 7 further comprising:
   means attached to said flexible base means for providing fibrogenic growth.

9. A body implantable lead according to claim 8 wherein said providing means includes surgical mesh.

* * * * *

REEXAMINATION CERTIFICATE (332nd)

United States Patent [19]

Stokes

[11] B1 4,313,448
[45] Certificate Issued Apr. 2, 1985

[54] MYOCARDIAL SUTURELESS LEAD

[75] Inventor: Kenneth B. Stokes, Brooklyn Park, Minn.

[73] Assignee: Medtronic, Inc., Minneapolis, Minn.

Reexamination Request:
No. 90/000,568, Jun. 6, 1984

Reexamination Certificate for:
Patent No.: 4,313,448
Issued: Feb. 2, 1982
Appl. No.: 115,966
Filed: Jan. 28, 1980

[51] Int. Cl.³ .............................................. A61N 1/04
[52] U.S. Cl. .............................. 128/785; 128/419 P
[58] Field of Search .................. 128/419 P, 639, 644, 128/784–786

[56] References Cited

U.S. PATENT DOCUMENTS

| | | |
|---|---|---|
| 3,978,865 | 9/1976 | Trabucco ............................ 128/419 |
| 4,010,758 | 3/1977 | Rockland et al. ................... 128/785 |
| 4,136,702 | 1/1979 | Trabucco ............................ 128/418 |
| 4,144,890 | 3/1979 | Hess .................................... 128/418 |
| 4,177,818 | 12/1979 | De Pedro ............................ 128/418 |

*Primary Examiner*—William E. Kamm

[57] ABSTRACT

Myocardial sutureless unipolar lead including an insulated conductor coil adjacent to a base pad, and a barbed electrode spaced adjacent to the base pad and connected to the conductor coil. The sutureless myocardial unipolar lead requires no stab wound or sutures for electrode placement and support. The barbed electrode is secured to the heart by gently pushing the tip into the myocardial tissue and the electrode is thereby secured to the myocardial tissue. The lead accepts a stiffening stylet for controlling the stiffness to aid in placement of the electrode within the myocardial tissue, and without the need for further insertion tool. The angle of the barbed electrode determines the specific application of the lead for ventricular or atrial pacing applications.

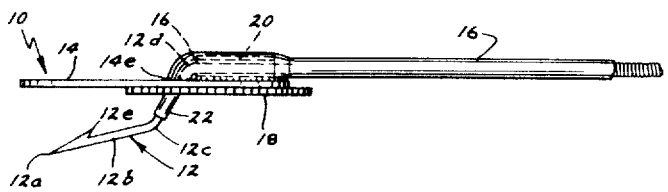

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-7 is confirmed.

Claims 8 and 9 are cancelled.

New claims 10-12 are added and determined to be patentable.

*10. A body implantable lead comprising:*
*a conductor having a distal end;*
*an insulating sheath covering said conductor;*
*electrode means attached to said conductor near said distal end for affixing said body implantable lead to body tissue and for stimulating said body tissue; and*
*flexible base means attached to said conductor near said distal end which in a relaxed state is disposed over said fixation means from at least one direction and which upon application of a small amount of force may be bent back exposing said electrode fixation means form said at least one direction.*

*11. A body implantable lead comprising:*
*a conductor having a distal end;*
*an insulating sheath covering said conductor;*
*electrode means attached to said conductor near said distal end for affixing said body implantable lead to body tissue said fixation means extending distal to said conductor; and*
*flexible base means attached to said conductor near said distal end which extends distal to said distal end of said conductor and which in a relaxed state is disposed over said electrode fixation means from at least one direction and which upon application of a small amount of force may be bent back exposing said electrode fixation means from said at least one direction.*

*12. A body implantable lead comprising:*
*a conductor having a distal end;*
*an insulating sheath covering said conductor;*
*electrode means attached to said conductor near said distal end for affixing said body implantable lead to body tissue; and*
*flexible base means attached to said conductor near said distal end which in a relaxed state is disposed over said electrode fixation means from at least one direction and which upon application of a small amount of force may be bent back exposing said electrode fixation means from said at least one direction; and*
*wherein said electrode fixation means includes a connecting shank coupled to said conductor and extending from said flexible base means and a tip shank extending from said connecting shank and angled toward said flexible base means.*

* * * * *